United States Patent [19]

Müller et al.

[11] 4,301,311

[45] Nov. 17, 1981

[54] PROCESS FOR THE PREPARATION OF DICYCLOPENTYLENE [2,2'-BIS(4-ALKYL-6-T-BUTYLPHENOLS)]

[75] Inventors: Rolf Müller, Polling; Werner Hartmann; Zdenek Kuca, both of Waldkraiburg, all of Fed. Rep. of Germany

[73] Assignee: Chemische Werke Lowi GmbH, Waldkraiburg, Fed. Rep. of Germany

[21] Appl. No.: 59,253

[22] Filed: Jul. 20, 1979

[30] Foreign Application Priority Data

Aug. 9, 1978 [DE] Fed. Rep. of Germany ....... 2834944
Oct. 4, 1978 [DE] Fed. Rep. of Germany ....... 2843323
Jul. 2, 1979 [DE] Fed. Rep. of Germany ....... 2926593

[51] Int. Cl.$^3$ ............................................. C07C 37/14
[52] U.S. Cl. .................................................. 568/719
[58] Field of Search ........................ 568/719, 792, 733

[56] References Cited

U.S. PATENT DOCUMENTS

2,385,787 10/1945 Bruson ................................. 260/612
3,305,522 2/1967 Spacht .............................. 260/45.95
3,751,375 8/1973 Bender et al. ......................... 260/2.5

FOREIGN PATENT DOCUMENTS

2201538 8/1972 Fed. Rep. of Germany ...... 568/719
1084390 7/1954 France ................................. 568/719

OTHER PUBLICATIONS

Olah Friedel–Crafts and Related Reactions I, 298–304 II 84 (1963).

*Primary Examiner*—Robert Gerstl

*Attorney, Agent, or Firm*—Oblon, Fisher, Spivak, McClelland & Maier

[57] ABSTRACT

The invention concerns a process for the preparation of dicyclopentylene [2,2'-bis(4-alkyl-6-t-butylphenols)] of the formula I

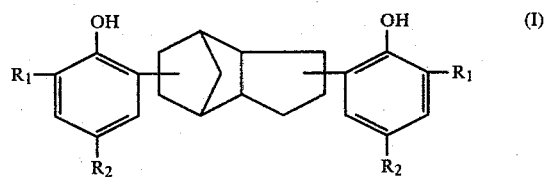

wherein
$R_1$ is tertiary butyl and
$R_2$ is methyl or ethyl, by the reaction of 1.5 to 2.5 moles of a 4-alkyl-6-t-butylphenol of the formula II

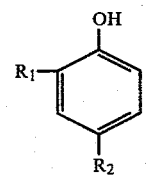

wherein $R_1$ and $R_2$ are as defined above, with 0.8 to 1.2 moles dicyclopentadiene at a temperature between 20° and 120° C. in the presence of an organic solvent and borontrifluoride or a complex thereof as catalyst, characterised by employment of specially selected solvents and reaction under practically anhydrous conditions.

9 Claims, No Drawings

PROCESS FOR THE PREPARATION OF DICYCLOPENTYLENE [2,2'-BIS(4-ALKYL-6-T-BUTYLPHENOLS)]

This invention relates to a process for the preparation of dicyclopentylene [2,2'-bis (4-alkyl-6-t-butylphenols)]. More particularly, the invention is concerned with the nature of solvents which can be employed in such process and reaction conditions.

A series of processes are known for the preparation of very different reaction products of phenol or substituted phenols and dicyclopentadiene.

In U.S. Pat. No. 2,385,787 there is described a process for producing a dihydro-norpolycyclopentadienyl ether from phenol or a substituted phenol, which comprises a reaction of dicyclopentadiene with a phenol or substituted phenol at temperatures between 25° and 50° C. in the presence of an acidic condensation agent, preferably a boron trifluoride-diethyl ether complex. The ethers obtained hereby are employed as insecticides, solvents, softeners or intermediates. By virtue of their lack of free phenolic hydroxy groups they are not suitable for use as anti-oxidants.

A process is known from French Pat. No. 1,084,390 for producing of cyclopentenylphenols and cyclopentylphenols, in which either the phenol ring is mono-, di-, or tri-substituted by cyclopentene or cyclopentane, or in which the cyclopentene ring is mono-substituted by phenol or the cyclopentane ring is di-substituted by phenol. This process comprises reaction of phenol or substituted phenol with cyclopentadiene in the presence of a Friedel-Craft catalyst, such as phosphoric acids, and optionally in the presence of a solvent such as touene, at temperatures between −20° C. and +100° C. Instead of cyclopentadiene one can here, amongst others, add dicyclopentadiene which under the reaction conditions of this process however is completely depolymerized into cyclopentadiene. Thus, in this reaction, no dicyclopentenyl or dicyclopentylene compounds can be formed, but only cyclopentene and cyclopentane compounds. The compounds obtained in this fashion are intended for use as fungicides, insecticides, herbicides and intermediates.

From U.S. Pat. No. 3,036,138, it is known to employ reaction products of dicyclopentadiene and phenol or substituted phenols as antioxidants for the stabilisation of latex rubber. The corresponding compounds are obtained by condensation of 1 mole of cyclopentadiene with at least 1 mole of phenol, which is optionally substituted by hydrogen, halogen, saturated or unsaturated hydrocarbon radicals or alkoxy radicals, at least one of the positions 2, 4, or 6 being occupied only by hydrogen, under such conditions that no depolymerisation of the dicyclopentadiene takes place. In this process, the reaction is carried out in the presence of a Friedel-Craft catalyst, preferably boron trifluoride or a boron trifluoride complex, at temperatures between 30° and 150° C. In accordance with the examples, the reaction can take place with or without solvent, and in the former case only toluene is employed as solvent. Products which should be obtained in accordance with this precedure are of the formula

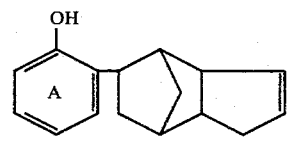

in which the benzene ring A may be substituted by saturated or unsaturated hydrocarbon radicals, halogen atoms or alkoxy groups, and in which there is at least one dicyclopentenyl radical. The condensation products obtained in accordance with this procedure should be more or less polymeric products. The process itself apparently proceeds in entirely uncontrolled fashion, since according to the examples, even when employing the same starting materials and otherwise the same reaction conditions, condensation products having totally different melting points are obtained. In this connection reference only needs to be made to Examples 1, 3 and 5. The production of a specific condensation product from a specific phenol and dicyclopentadiene is not possible. The condensation products obtained are of course active as anti-oxidants, but are not as active as corresponding reaction products obtained in accordance with a special two-step process such as is described in German Pat. No. 1,495,985. In particular, reference is made to comparative tests in the German Pat. No. 1,495,985 concerning anti-oxidant activities of such products.

The German Pat. No. 1,495,985 is directed to a process for producing polyadducts of phenolic compounds and dicyclopentadiene, which consists therein that a reaction product obtained in known manner by reaction of 1.0 to 5 moles of phenolic compound, which can be phenol, p-cresol, a mixture of m- and p-cresol or p-ethylphenol, at a temperature between 25° and 160° C., with 1 mole of dicyclopentadiene in the presence of 0.1 to 5% by weight of boron trifluoride, based on the total weight of starting material components, is alkylated with at least half a mole, based on 1 mole of dicyclopentadiene, of iso-butylene, tertiary pentene or tertiary hexene, at a temperature between 20° and 100° C. in the presence of 0.1 to 5% by weight of an alkylation catalyst, based on the total weight of the reaction products. Instead of boron trifluoride and complexes based on boron trifluoride, the first stage of the above reaction can also be carried out in the presence of other Friedel-Craft catalysts, in particular stronger Friedel-Craft catalysts such as aluminium chloride, zinc chloride, ferrous chloride or ferric chloride. However, it is preferred to employ a boron trifluoride-phenol complex in the first stage of the reaction. The first stage of the reaction can be carried out in the presence or absence of an organic solvent, the only solvents which are mentioned however being benzene or toluene.

For the second stage of the reaction in which the reaction product of the first stage of the reaction is alkylated, it is also possible to employ boron trifluoride or a complex based on boron trifluoride. However, it is preferred that such catalyst which is essential in the first stage of the reaction, be removed and replaced by a typical alkylation catalyst, such as sulfuric acid, since otherwise an increased number of undesirable side reactions take place. The second stage of the reaction can also be carried out in the presence or absence of an organic solvent. Here, the same solvents as may be employed in the first stage of the reaction come into question.

The products which may be obtained in accordance with the process described in German Pat. No. 1,495,985 are highly complex reaction product mixtures of relatively high molecular weight, which cannot be described by a definite chemical formula and from which mixtures no chemically pure compounds can be isolated. They can accordingly not be described in terms of an accurate chemical formula and can not be named in terms of standard chemical nomenclature. Accordingly, it is also not possible to obtain defined reaction products of phenolic compounds and dicyclopentadiene in a precisely defined fashion by means of this special process. Thus, the same situation exists as already discussed in connection with U.S. Pat. No. 3,036,138.

The complexity and variablity of reaction products produced in accordance with U.S. Pat. No. 3,036,138 and German Pat. No. 1,495,985 can furthermore be seen from the fact that the latter products are significantly more active antioxidants for latex rubber than the first products. Namely, proceeding from the substituted phenol which is already substituted in the ring by tertiary hydrocarbon radicals through the one-step reaction with dicyclopentadiene in accordance with U.S. Pat. No. 3,036,138, a reaction product is obtained which is significantly less active than the reaction product obtained in accordance with the two-step process described by German Pat. No. 1,495,985 and wherein the phenol which is not already substituted by tertiary hydrocarbon radicals is reacted with dicyclopentadiene and the reaction product obtained is then in a second step alkylated by introducing tertiary hydrocarbons into the ring of the phenol which is present. Determinative for the formation of such complex reaction products having particularly good anti-oxidant activity is thus apparently employment of a very precise and special procedure.

This process leads to products which are very active anti-oxidants for latex rubber, but the products have a serious disadvantage in that an extremely laborious two-step process is involved which does not enable a specific product to be produced from specific phenols and dicyclopentadiene. These advantages have hitherto been accepted since the polyadducts which may be obtained in accordance with German Pat. No. 1,495,985 being to the best antioxidants of their time for organic polymers.

The invention accordingly has the object of establishing a new process for producing compounds suitable as anti-oxidants, which can be carried out in a single step by reaction of 4-alkyl-6-t-butylphenol with dicyclopentadiene at high yield to obtain a well-defined practically consistent and thereby non-polymeric product with comparable or better anti-oxidant activity than products which can be obtained by the laborious two-step process, in particular as is possible in accordance with the above German Pat. No. 1,495,985.

This object, in accordance with the invention, is solved by a process for the preparation of dicyclopentylene[2,2'-bis(4-alkyl-6-t-butylphenols)] of the formula I

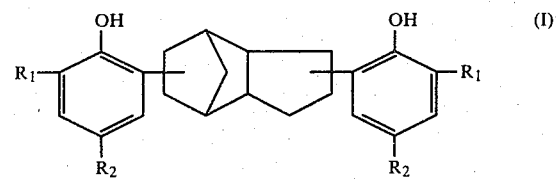

wherein
$R_1$ is tertiary butyl and
$R_2$ is methyl or ethyl,
by the reaction of 1.5 to 2.5 moles of a 4-alkyl-6-t-butyl-phenol of the formula II

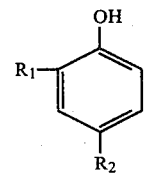

wherein $R_1$ and $R_2$ are as defined above,
with 0.8 to 1.2 moles dicyclopentadiene at a temperature between 20° and 120° C. in the presence of an organic solvent and borontrifluoride or a complex thereof as catalyst, characterised in that the solvent is selected from:
 (a) an aromatic solvent which does not enter into any significant trans-alkylation with the teritary butyl group of the 4-alkyl-6-t-butyl-phenol under the reaction conditions in the presence of the catalyst,
 (b) a non-aromatic solvent which does not possess significant nucleophilic properties which strongly reduces or practically eliminates the activity of the catalyst, or
 (c) a mixture of (a) and (b)
and that the reaction is carried out under practically anhydrous conditions.

The process of the invention is preferably carried out by employing a mole ratio of 1.8 to 2.2 moles of 4-alkyl-2-t-butyl phenol of the formula II and from 0.9 to 1.1 moles of dicyclopentadiene.

Of course the above process must be carried out under conditions which will not lead to any depolymerisation of the dicyclopentadiene employed as starting material, since this tricyclic ring is an important component of the compound to be produced.

The reaction temperature can in general lie between 20° and 120° C., but is preferably between 30° and 95° C. It is best to initiate the reaction in the region of the lower temperatures, for example at 30° to 40° C., and then to allow the temperature to increase during the course of the reaction to the desired end temperature, for example 80° and 95° C.

Examples of particularly suitable catalysts in the process of the invention are complexes of boron trifluoride and p-cresol, boron trifluoride and phenol or boron trifluoride and diethylether or boron trifluoride gas directly. The corresponding catalyst is employed in conventional amounts and thus the reaction is preferably carried out with 0.1 to 8% by weight, particularly 0.5 to 5% by weight.

An important factor for the success of the above reaction is the employment of a particular solvent. The solvent to be employed may not react with the reactants or the catalysts and may neither affect the reaction mechanism nor lead to side-reactions. The solvent should furthermore also simultaneously lend itself to the removal of water comprised in the reactants and other components of the reaction mixture by azeotropic distillation.

Where an aromatic solvent is employed, it must be ensured, as already mentioned, that the solvent does not lead to transalkylation with the tertiary butyl group of the 4-alkyl-6-t-butyl phenol of the general formula II.

Aromatic solvents belonging to such include amongst others xylenes, trimethyl benzenes, tetramethyl benzenes, pentamethyl benzenes, chloro-benzene, dichlorobenzene, nitro-benzene or benzonitrile, in general, 1,3-xylene, 14-xylene, 1,3,5-trimethyl benzene, chlorobenzene, 1,2-chloro-benzene, 1,4-dichlorobenzene and nitrobenzene being preferred.

Benzene and toluene are only of limited suitability as aromatic solvents, since as a result of trans-alkylation they lead to a deterioration of product and a loss in yield. For example, in a reaction of 4-methyl-6-t-butyl phenol with dicyclopentadiene in accordance with the above process, in the presence of benzene or toluene as solvent which is not in accordance with the invention, a high loss in yield of desired product occurs through transalkylation of the t-butyl group of the phenol of the general formula II with the formation amongst others of t-butyl benzene or p-t-butyl toluene.

As also already mentioned, the non-aromatic solvents which are employed should not possess significant nucleophilic properties under the reaction conditions which strongly reduces or practically eliminates the activity of the catalyst, which thereby necessitates use of a solvent which does not form free protons under the reaction conditions, since otherwise undesirable substances are formed which reduce the yield and lead to a lowering of the quality of the product.

Non-aromatic solvents which belong to the group of solvents according to the invention include in general alkanes, preferably n-alkanes having 5 to 12 carbon atoms per molecule, such as n-hexane, n-heptane or petroleums having a boiling point of about 80° to 170° C., halogenated alkanes, preferably having 1 to 3 carbon atoms per molecule, such as dichloro-methane, chloroform, carbon tetrachloride, dichloroethane, trichloroethane, tetrachloroethane, dichloethylene, trichloroethylene or tetrachloroethylene, cycloalkanes, preferably having 5 to 12 carbon atoms per molecule, such as cyclopentane, open chain ethers, such as diethylether or dipropyl ether, cyclic ethers, such as tetrahydrofuran, tetrahydropyran or dioxane, or also solvents such as acetonitrile, dimethyl formamide, dimethylacetamide, dimethylsulfoxide, tetramethylurea or tetrahydrothiophene-1,1-dioxide, or also the various ethylene glycol ethers (Cellosolve) such as ethylglycol acetate or methyl glycol acetate.

A particularly important factor of the process of the invention is that the reaction be carried out under practically anhydrous conditions. If the reaction is not carried out with the exclusion of water, impure products and by-products are formed, which leads to significant difficulties in working up the desired product or that such is not obtained at all in the desired amount. As already mentioned above, the formation or presence of free proton donor substances is to be avoided in the above reaction, and such can already take place in the presence of even the smallest amounts of water. In the process of the invention, therefore, the amount of water should be maintained as low as is practically possible, since even the smallest amount in the reaction mixture already leads to a notable loss in yield and deterioration of purity of the product and its quality. The above reaction should therefore in general be carried out with water contents which are below 0.1% by weight, preferably below 0.05% by weight, and especially below 0.025% by weight. The necessary reaction under practically anhydrous conditions can for example be achieved by rendering the reactants, namely the corresponding 4-alkyl-6-t-butyl phenol of the formula II, the dicyclopentadiene, the corresponding catalyst and the solvent practically water-free in manner known to those skilled in the art, before the actual reaction is commenced. This can for example be practiced by freeing the individual reactants from water individually in conventional manner, or by carrying out an azeotropic distillation with the reaction mixture in the absence of the catalyst but in the presence of the solvent before commencement of the reaction. For such an azeotropic distillation, it is best to employ the same solvent as will also be employed in the reaction itself. After removal of the undesirable water, the actual reaction is then carried out by the addition of the corresponding catalyst and optionally also then the practically water-free dicyclopentadiene.

The dicyclopentylene [2,2'-bis(4-alkyl-6-t-butyl phenols)] of said formula I which can be obtained in accordance with the above process possess excellent anti-oxidant activity, so that they are particularly suitable as anti-oxidants for organic substances. They are as good as or even better than the polyadducts which may be obtained in accordance with German Pat. No. 1,495,985 from phenolic compounds and dicyclopentadiene in their anti-oxidant activity. Furthermore they have the advantage over these products that they can be obtained by a much simpler one-step process and represent uniform pure products which practically do not discolour with time. The dicyclopentylene [2,2'-bis(4-alkyl-6-t-butyl phenols)] obtained by the process of the invention accordingly do not need to be subjected to laborious special cleansing operations in order to improve their colour, such as is recommended for the products of the U.S. Pat. Nos. 3,036,138 and 3,305,522 (German Pat. No. 1,495,985) in German Patent application No. 2,201,538.

For the stabilisation of organic polymers against an oxidiative deterioration, the above products are usually added in amounts of from 0.5 to 8 parts by weight, preferably 0.1 to 3.0 parts by weight, for each 100 parts by weight of the substances to be stabilised. They can of course also be combined with other anti-oxidant substances for this purpose.

Examples of organic substances in which the above products can be employed with success are natural rubber and their vulcanisates, optionally blended with other polymers, natural latex and so-called rubber solutions based on natural rubber, synthetic rubber such as styrene/butadiene rubber, butadiene rubber, isoprene rubber, acrylonitrile/butadiene rubber, chloroprene rubber, rubbers based on ethylene/propylenediene terpolymers, isobutylene/isoprene rubbers as well as their vulcanisates, lattices and solutions, polyamide resins, vegetable oils, mineral oils, polyolefins, polyacetates and polymers thereof, saturated and unsaturated polyesters as well as polystyrols.

The compounds obtained in accordance with the invention can be employed as anti-oxidants for the stabilisation of all organic materials which have already been stabilised with known antioxidants.

The invention will further described by means of the following examples:

EXAMPLE I

To a flask equipped with a condenser, stirrer and water-remover, 730 g of 4-methyl-6-t-butyl phenol and 200 g of n-hexane are added. The entire mixture is heated to condensation temperature until such time as the water-content in the flask is below 0.05% by weight. Then, under the action of vigorous stirring, 25 g of a boron trifluoride-phenol complex is added and thereafter the whole mixture is reacted with 440 g of practically water-free dicyclopentadiene in such a fashion that the reaction mixture does not reach a temperature in excess of 95° C. Thereafter, the reaction mixture is washed by the addition of 200 g of an aqueous saturated sodium carbonate solution, in which the aqueous phase is removed. The resulting non-aqueous phase is first distilled under normal pressure to remove the n-hexane, whereby one attains 195 g of n-hexane. Then the remaining material is subjected to a distillation at a pressure of 10 atmospheres at a temperature of 160° C. In this manner, one obtains 1106 g (yield 94%) of a bright yellow mass which solidifies upon cooling. This mass melts at a temperature of 118° to 120° C. A suitable IR and NMR spectroscopical analysis reflects that the compound obtained is of the following structural formula:

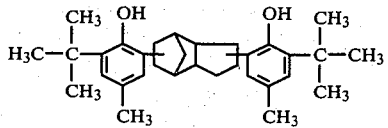

A residue of 6 g of a material remains after the above distillation, which following on an analysis reveals that this consists of p-cresol (4-methylphenol) originating side products.

EXAMPLE 2

To a flask equipped with a condenser, stirrer and water-remover, there is added 344 g of 4-methyl-6-t-butyl phenol and 91 g of an aromatic free petroleum (boiling point region 140° to 160° C.). The mixture is heated at condensation temperature until such time as the water-content in the flask is less than 0.05% by weight. Then, under the action of vigorous stirring, 113 g of boron trifluoride-phenol complex is added and the whole is then reacted with 132 g of practically water-free dicyclopentadiene under such conditions that the reaction mixture does not reach a temperature in excess of 85° C. The reaction mixture is then washed by the addition of 90 g of an aqueous satuared solution of sodium carbonate, in which the watery phase is removed. The resulting non-aqueous phase is then distilled under normal pressure to remove the petroleum, whereby 88 g of petroleum is obtained. The remaining material is then distilled under a pressure of 2 atmospheres at a temperature of 200° C. In this fashion 450 g (yield 94%) of a bright yellow mass is obtained which solidifies upon cooling. The melting point of this mass is 120° to 122° C. An appropriate IR and NMR spectroscopic analysis reveals that a compound of the same structure as shown in Example 1 is obtained.

EXAMPLES 3 to 14

The procedure described in Example 1 is repeated with a water-content of below 0.05% by weight and at a temperature not in excess of 80° C., with other solvents in amounts each time of 200 g, whereby the results shown in the following Table 1 are obtained:

TABLE I

| Example | Solvent | Product yield (g) | Product yield (% by weight) | Recovered solvent amount (g) | By-products from p-cresol (g) | Product properties melting point (°C.) | appearance |
|---|---|---|---|---|---|---|---|
| 3 | n-heptane | 1110 | 94,8 | 193 | 60 | 119 to 120° | not tacky |
| 4 | petroleum (b.p. 80-110° C., aromatic content <0.1) | 1105 | 94,4 | 194 | 65 | 119 to 212° | " |
| 5 | petroleum (b.p. 100-140° C., aromatic content <0.1) | 1108 | 94,7 | 195 | 62 | 118 to 120° | " |
| 6 | petroleum (b.p. 140-170° C., aromatic content <0.1) | 1106 | 94,5 | 194 | 64 | 120 to 122° | " |
| 7 | cyclohexane | 1105 | 94,4 | 193 | 63 | 118 to 120° | " |
| 8 | mixture of cyclohexane, n-hexane & n-heptane (prop. by weight 1:1:1) | 1106 | 94,5 | 193 | 61 | 117 to 119° | " |
| 9 | carbon tetrachloride | 1107 | 94,5 | 195 | 63 | 117 to 120° | " |
| 10 | 1,3,5-trimethyl benzene | 1103 | 94,2 | 194 | 65 | 116 to 118° | " |
| 11 | 2,4-xylene | 1103 | 94,2 | 192 | 70 | 116 to 119° | " |
| 12 | chlorobenzene | 1105 | 94,4 | 195 | 68 | 118 to 121° | " |
| 13 | diethylether | 1102 | 94,1 | 190 | 67 | 116 to 120° | " |
| 14 | acetonitrile | 1095 | 93,6 | 192 | 72 | 116 to 118° | " |

EXAMPLE 15

The procedure described in Example 1 is repeated, with less than 0.05% by weight water content and at a temperature not in excess of 80° C., however, with the employment of boron trifluoride gas as catalyst, whereby 1135 g (yield 97.0%) of the desired product is obtained, which possesses a melting point of 116° to 119° C. and is not tacky.

EXAMPLES 16 and 17

The procedure described in Example 1 is repeated, with less than 0.05% by weight water content, but at other reaction temperatures, whereby the results shown in Table II are obtained:

| Example | Reaction temperature (°C.) | Product yield (g) | Product yield (% by weight) | Product properties melting point (°C.) | Product properties appearance |
|---|---|---|---|---|---|
| 16 | 30 to 40 | 1099 | 93,9 | 116 to 119 | not tacky |
| 17 | reaction commenced at 40, reaction terminated at 80 | 1102 | 94,1 | 117 to 119 | not tacky |

EXAMPLES 18 to 20

The procedure described in Example 1 is repeated, at water contents of 0.08% by weight, 0.05% by weight at a temperature not in excess of 80° C., whereby the results shown in the following Table III are obtained:

TABLE III

| Example | Water-content (% by weight) | Product yield (g) | Product yield (% by weight) | Unusable side products (g) | Unusable side products (% by weight) | Product properties melting point (°C.) | Product properties appearance |
|---|---|---|---|---|---|---|---|
| 18 | 0,08 | 1101 | 94,0 | 63 | 5,5 | 115 to 118 | not tacky |
| 19 | 0,04 | 1095 | 93,5 | 71 | 6,1 | 116 to 119 | " |
| 20 | 0,01 | 1106 | 94,5 | 64 | 5,5 | 118 to 120 | " |

EXAMPLE 21

To a flask equipped with a condenser, stirrer and funnel, 730 g of 4-methyl-6-t-butyl phenol and 200 g of n-hexane are added. Both products are pre-dried to a water-content of 0.07% by weight. The mixture is warmed to 40° C., and 25 g of a boron trifluoridephenol complex is added in one shot. Then 440 g of practically water-free dicyclopentadiene is added dropwise through the funnel within a period of an hour. The reaction temperature is controlled so that is does not exceed 80° C. during this addition. After working up the reaction mixture as described in Example 1, 110 g of a bright yellow mass is obtained having a melting point of 117° to 119° C.

COMPARATIVE EXAMPLE 1

The procedure described in Example 1 is followed in detail, except that 200 g of toluene is employed as solvent in place of n-hexane. With a corresponding removal of the toluene by distillation under normal pressure, only 94 g of the 200 g added is recovered. After distillation of the remaining mass (10 atmospheres/160° C.) a residue of 901 g results. This, initially, amounts to a yield of 77%. The melting point of the material can not be determined and it possesses a broad temperature range of softening between 92° to 105° C. A gas chromatographic examination of the distillate shows that, other than 31 g of p-cresol and 64 g of non-definable substances, 172 g of a substance is present which, on the basis of gas chromatographic analysis, reveals that this is essentially p-t-butyl toluene. As a result of the use of toluene as solvent, a high loss in yield occurs and the formation of a series of undesirable products are obtained by virtue of a trans-alkylation having taken place.

COMPARATIVE EXAMPLE 2

The process described in Example 1 is followed in detail, excepting that water is not removed before the reaction by azeotropic distillation. After an appropriate working up of the reaction mixture, 673 g (yield 57.5%) of a residue is obtained, which solidifies into a slightly tacky mass. The melting point of this mass can not be determined and lies between 72° and 85° C. On the basis of corresponding IR and NMR spectroscopic examinations, the product obtained is of undefinable constitution.

COMPARATIVE EXAMPLES 3 AND 4

The process of Example 1 is repeated with a water-content of less than 0.5% by weight and at a temperature not exceeding 80° C., in which however benzene or a 1:1 parts by weight of a mixture of n-hexane and toluene is employed. The results obtained can be seen from the following Table IV:

TABLE IV

| Comparative Example No. | Solvent | Product yield (g) | Product yield (% by weight) | Recovered solvent (g) | By-products originating from p-cresol solvent (g) | By-products originating from p-cresol solvent (g) | Product properties melting point (°C.) | Product properties appearance |
|---|---|---|---|---|---|---|---|---|
| 3 | benzene | 922 | 78,8 | 112 | 163 | 168 | 88 to 103 | tacky |
| 4 | mixture of n-hexane & toluene (100:100 Parts by weight) | 933 | 79,7 | 97:48 | 196 | 86 | 93 to 105 | " |

COMPARATIVE EXAMPLE 5

The procedure of Example 1 is repeated at a temperature not exceeding 80° C., however with a water-content of 0.3% by weight, whereby 600 g (yield 51.3% by weight) of product is obtained, which product melts in the range of 60° to 75° C. and is strongly tacky. A residue of 570 g (48.7% by weight) of unusable byproducts results.

COMPARATIVE EXPERIMENTS

The anti-oxidant activity of the discyclopentylene [2,2'-bis (4-alkyl-6-t-butyl phenol)] obtained in accordance with the invention is compared with the anti-oxidant activity of products of the state of the art which have not been produced in accordance with the invention, by the known procedure of determinating the oxygen absorption of polymers. Here, in each case, 1 part by weight of the corresponding anti-oxidant is added to 100 parts by weight of the corresponding polymer. The resulting samples are then exposed to a pure oxygen atmosphere at constant temperature (100° C.), and the time that it takes for the sample to take up 1% by weight of oxygen is measured. As polymer, a non-stabilised styrene/butadiene rubber made up of 75 parts by weight of butadiene and 25 parts by weight of styrene, is employed. The test results obtained hereby can be seen from the following Table V:

TABLE V

| Experiment No. | Anti-oxidant | Time taken for absorption of 1% by weight of oxygen (hours) |
|---|---|---|
| 1 | Example 1 | 197 |
| 2 | Example 2 | 199 |
| 3 | Example 3 | 197 |
| 4 | Example 4 | 198 |
| 5 | Example 5 | 197 |
| 6 | Example 6 | 199 |
| 7 | Example 7 | 197 |
| 8 | Example 8 | 197 |
| 9 | Example 9 | 197 |
| 10 | Example 10 | 196 |
| 11 | Example 11 | 196 |
| 12 | Example 12 | 198 |
| 13 | Example 13 | 197 |
| 14 | Example 14 | 194 |
| 15 | Example 15 | 195 |
| 16 | Example 16 | 195 |
| 17 | Example 17 | 197 |
| 18 | Example 18 | 193 |
| 19 | Example 19 | 193 |
| 20 | Example 20 | 197 |
| 21 | Example 21 | 197 |
| 22 | Comparison Example 1 | 171 |
| 23 | Comparison Example 3 | 168 |
| 24 | Comparison Example 4 | 175 |
| 25 | None | 21 |
| 26 | Product of Example 1 of German Patent 1,495,985 | 181 |
| 27 | WING STAY L (Goodyear) | 185 |
| 28 | PLASTINOX 2246 (American Cyanamid Company) 2,2'-methylene-bis(4-methyl-6-t-butylphenol) | 148 |
| 29 | 2,2'-isobutylidene-bis(4,6-dimethylphenol) | 135 |

The anti-oxidant activity of the dicyclopentylene [2,2'-bis(4-alkyl-6-t-butyl phenols)] obtained by the invention are also compared with known anti-oxidants for their ageing properties by means of a test on a latex foam. For preparing such latex foam, one proceeds from the following composition.

TABLE VI

| Materials | Parts by weight |
|---|---|
| Bunatex K 17[(1)] | 100 |
| Vulcanisation paste Suprotex[(2)] | 7 |
| Slipol KG[(2)] | 3 |
| Anti-oxidant Dispersion (50%) | 2 |
| Natriumsiliconefluoride | 6 |

[(1)]Buna-Werke Huls
[(2)]Weserland KG

The latex foams prepared from above composition are stored in an air cupboard at 120° C., and the time is recorded that it takes for the foams to become clearly brittle or friable. The results obtained hereby can be seen from the following Table VII:

| Experiment No. | Anti-oxidant | Time taken for foam to become friable (days) |
|---|---|---|
| 1a | Example 1 | 26 |
| 2a | Example 2 | 27 |
| 25a | None | 6 |
| 26a | Product of Example 1 of German Patent 1,495,985 | 24 |
| 27a | WING STAY L (Goodyear) | 25 |
| 28a | PLASTINOX 2246 (American Cyanamid Company) 2,2'-methylene-bis(4-methyl-6-t-butylphenol) | 20 |
| 29a | 2,2'-Isobutylidene-bis(4,6-dimethylphenol) | 21 |

The above comparative values show that the compounds which can be obtained in accordance with the invention are as good as or better than known anti-oxidants in their stabilising properties of organic substances.

What we claim is:

1. A process for the preparation of dicyclopentylene [2,2'-bis(4-alkyl-6-t-butylphenols)] of the formula I

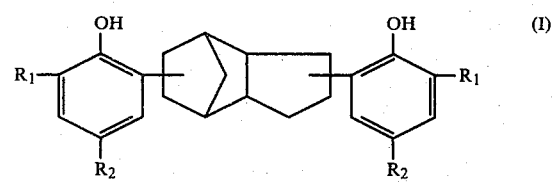

wherein
$R_1$ is tertiary butyl and
$R_2$ is methyl or ethyl,
by the reaction of 1.5 to 2.5 moles of a 4-alkyl-6-t-butylphenol of the formula II

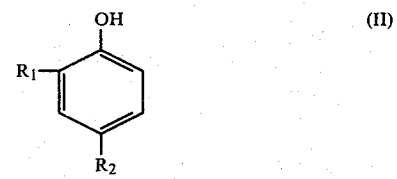

wherein $R_1$ and $R_2$ are as defined above, with 0.8 to 1.2 moles dicyclopentadiene at a temperature between 20° and 120° C. in the presence of an organic solvent and borontrifluoride or a complex thereof as catalyst, characterised in that the solvent is selected from:

(a) an aromatic solvent which does not enter into any significant trans-alkylation with the tertiary butyl group of the 4-alkyl-6-t-butyl-phenol under the reaction conditions in the presence of the catalyst, (b) a non-aromatic solvent which does not possess significant nucleophilic properties which strongly reduces or practically eliminates the activity of the catalyst, or (c) a mixture of (a) and (b)

and that the reaction is carried out under practically anhydrous conditions.

2. A process according to claim 1, characterised in that an aromatic solvent is employed which is selected from 1,3-xylene, 1,4-xylene, 1,3,5-trimethylbenzene, chlorobenzene, dichlorobenzene, nitrobenzene, or mixtures thereof.

3. A process according to claim 1, characterised in that a non-aromatic solvent is employed which is selected from an alkane, a halogenated alkane, a cycloalkane, an open-chain ether, a cyclic ether, or mixtures thereof.

4. A process according to claim 3, characterised in that the non-aromatic solvent is an n-alkane or a cycloalkane having 5 to 12 carbon atoms in the molecule.

5. A process according to claim 3, characterised in that the solvent is selected from n-hexane, n-heptane, a petroleum having a boiling point of about 80° to 170° C., carbon tetrachloride, cyclohexane, diethyl ether or acetonitrile.

6. A process according to claim 1, characterised in that the water-content of the reaction mixture is up to 0.1% by weight.

7. A process according to claim 6, in which the water-content is up to 0.05% by weight.

8. A process according to claim 7, in which the water-content is up to 0.025% by weight.

9. The process of claim 1, wherein $R_2 = -CH_3$.